United States Patent [19]

Goering et al.

[11] 4,311,714

[45] Jan. 19, 1982

[54] PRODUCTION OF PRODUCTS FROM WAXY BARLEY GRAIN

[75] Inventors: Kenneth J. Goering; Robert F. Eslick, both of Bozeman, Mont.

[73] Assignee: Endowment and Research Foundation at Montana State University, Bozeman, Mont.

[21] Appl. No.: 47,855

[22] Filed: Jun. 12, 1979

[51] Int. Cl.³ .............................. A23L 1/09; A23J 1/12
[52] U.S. Cl. ........................................ 426/28; 426/52;
127/38; 127/42; 260/112 G
[58] Field of Search ...................... 426/18, 28, 31, 52;
435/74, 99

[56] References Cited

U.S. PATENT DOCUMENTS

| | | | |
|---|---|---|---|
| 2,583,684 | 1/1952 | Christensen | 435/99 |
| 3,115,410 | 12/1968 | Huffman | 252/316 |
| 3,791,865 | 2/1974 | Hurst et al. | 127/32 |
| 3,998,696 | 12/1976 | Yomoto et al. | 435/99 X |
| 4,012,333 | 3/1977 | Towle | 426/573 |
| 4,042,414 | 8/1977 | Goering et al. | 127/32 |
| 4,069,103 | 1/1978 | Muller | 435/99 X |
| 4,116,770 | 9/1978 | Goering et al. | 435/99 X |
| 4,125,528 | 11/1978 | Rao et al. | 260/112 G |
| 4,154,623 | 5/1979 | Schwengers et al. | 127/39 |

FOREIGN PATENT DOCUMENTS 652194  4/1951  United Kingdom ................ 435/99

OTHER PUBLICATIONS

Noyes, R., "Protein Food Supplements", Noyes Dev. Corp., Park Ridge, N.J., 1969, pp. 276, 277.
W. Banks et al., "Studies on the Starches of Barley Genotypes: the Waxy Starch", Die Stärke, vol. 22, No. 5, May 1970, pp. 149-152.
M. A. Anderson et al., "Enzymatic Determination of 1,3:1,4-A-Glucans in Barley Grain and Other Cereals", Journal of the Institute of Brewing, vol. 84, Jul.-Aug. 1978, pp. 233-239.
C. C. Calvert et al., "Waxy vs. Normal Barley in Rat and Pig Diets", Chemical Abstracts, vol. 86, No. 19, p. 437, No. 138444e.

*Primary Examiner*—Robert A. Yoncoskie
*Attorney, Agent, or Firm*—Lowe, King, Price & Becker

[57] ABSTRACT

The processing of barley grain by a series of sequential steps to produce a carbohydrate syrup having a high maltose content, novel protein products, a gluten-like product, a carbohydrate gum, all useful in the food industry, and a fermentable product which can be converted to alcohol. The processing steps comprise conditioning and milling, separation of starches, conversion of starch residues to the syrup and protein products, and recovery of the products and by-products.

29 Claims, 5 Drawing Figures

PRODUCTION OF PRODUCTS FROM WAXY BARLEY GRAIN

TECHNICAL FIELD

This invention relates to the processing of waxy barley grain to obtain valuable products therefrom and more particularly, to the processing of waxy barley grain for the production of a carbohydrate syrup high in maltose content, a variety of protein products, a fermentable product suitable for conversion to alcohol, a carbohydrate gum and novel uses for these products.

BACKGROUND ART

Barley is a grain product which has been found useful mainly in the brewing industry as barley malt which utilizes the enzymatic activity of the barley malt for industrial applications such as starch-splitting and protein degrading. The barley malt is an important source of alpha- and beta-amylase and is used in many foods such as beer, wheat flour and cereal to convert starch to fermentable sugars. Exemplary prior art showing the use of barley in the formation of malts and the use of malts in the fermentable industry may be found for example in U.S. Pat. Nos. 2,947,667, 3,157,583, 3,446,708 and 4,140,802.

There has been very limited work in the utilization of barley in other areas heretofore. Exemplary of the prior art in which there have been attempts to use barley in other ways be exemplified by U.S. Pat. No. 3,846,397 which processes grain residues obtained from mashed barley malt to recover water soluble protein products suitable for utilization as animal feeds.

U.S. Pat. No. 1,548,721 is also of interest as it describes the treatment of starch with an ungerminated grain such as barley until the major portion of the starch has been saccharified. However, useful products are not obtained from the barley in this procedure.

U.S. Pat. No. 3,689,277 discloses production of a protein hydrolysate from barley grain by treating with a proteolytic enzyme at 35°-50° C. to produce protein hydrolysis products and a starch fraction, the solution containing at least 40% of protein. The protein is then reacted with sugar to produce a product having a caramel flavor.

U.S. Pat. No. 3,901,725 describes wet processes for separating cereal starch granules according to size and states that barley, rye and wheat starch may be treated in the process. However, the patent does not set forth specific examples of obtaining any product from a barley grain. U.S. Pat. No. 4,094,700 is directed to a method for producing gluten and starch from a dispersion of wheat, barley or rye endosperm fractions in water. However, there is no actual example directed to processing of barley as the starting material or any description of a product obtained from barley.

A publication entitled "Barley Syrup Production" by The ABMIP/DDS-KROYER Process, Phamphlet No. 815G008E, published by the Danish Company, DDS-KROYER, presented in 1972 in Peking by Erik S. Nilsson, discloses the conventional procedure for processing of barley by conversion to malt through germination of the raw barley. A process is disclosed wherein an extract simulating the extract from barley malt action can be produced by degrading barley directly with enzymes such as alpha-amylase or beta-amylase.

U.S. Pat. No. 3,791,865 discloses maltose syrups obtained from corn starch wherein the syrup contains 60–80% maltose and 15–35% maltotriose.

DISCLOSURE OF INVENTION

It is accordingly one object of the present invention to provide a series of processing steps by which a number of valuable products can be obtained from waxy barley grain, which products have not been known heretofore.

A still further object of the invention is to provide a manufacturing process for treating raw waxy barley grain to produce a carbohydrate syrup which is high in maltose content, and which is useful in numerous areas of the food industry.

A still further object of the present invention is to provide a method for processing of waxy barley grain to produce a high maltose carbohydrate syrup, low, medium, or high protein-content products, some of which have the characteristics of gluten, a by-product suitable for fermentation to produce alcohol, and a carbohydrate gum.

A still further object of the invention is to provide a complete processing system by which these products can be obtained utilizing a continuous procedure whereby the products are obtained in sufficient purity to be used in a wide spectrum of food industry products.

Other objects and advantages of the present invention will become apparent as the description thereof proceeds.

BRIEF DESCRIPTION OF DRAWINGS

Reference is now made to the drawings accompanying the application wherein.

BEST MODE FOR CARRYING OUT THE INVENTION

In satisfaction of the foregoing objects and advantages there is provided by this invention a manufacturing process for the recovery of a number of valuable products from waxy barley starting materials or grain, said products comprising at least three different protein products including; (a) a gluten type product having a protein content of above about 80% with characteristics making it suitable for bread making and the like; (b) a bleached type protein product with a protein content in the range of about 70–78% which can be obtained in powdered form for use in food grade products for example as a substitute for soy protein; and (c) a protein residue containing from about 20–25% protein which is useful for incorporation in animal feeds. Also obtained as a result of the process is a barley syrup having a maltose content in excess of 60% and less than 5% dextrose which can be substituted for corn syrup and/or ordinary sugar in food products. A by-product liquid suitable for fermentation to alcohol is also produced together with by-products such as bran and carbohydrate gum.

The manufacturing process comprises treatment of waxy barley grain, that is, a barley grain which contains at least about 92% amylopectin, the steps of the process broadly comprising; (1) grinding the waxy barley grain and separating the bran to produce a barley flour; (2) mixing the flour with water and adding an enzyme; (3) milling the resulting mixture; (4) screening the milled mixture to produce, (a) a liquid which comprises a crude starch, and (b) solids which are mixed with water from the centrifuge and remilled; (5) adjusting the solids content of the starch product and adding an enzyme to effect starch conversion and form a paste by heating at a temperature of about 75°–76° C.; (7) cooling to about 40° C., adding additional enzyme and holding at about 40° C. for 1–4 hours; (8) heating to 60° C. and separating a protein product; (9) removing the residual beta-glucan partially hydrolyzed and released by the enzyme; (10) holding at about 60° C. for 18–48 hours until starch conversion is completed; (11) clarifying and separating solids, and (12) obtaining the maltose syrup carbohydrate concentrate.

The present invention is concerned with a series of processing steps by which a number of novel products are obtained from waxy barley grain which find value in various areas in industry. In particular, the process provides a procedure for producing high maltose syrup, at least three different protein-containing products, bran, a product suitable for fermentation in the formation of alcohol, and a beta-glucan, a carbohydrate gum, which may be used as a thickening agent in food preparations. The process is directed to the production of these products from waxy barleys, several strains of which are known in the art. The waxy barleys are chemically the same as starch found in waxy varieties of corn but the physical properties of the waxy barley starch are different from those of ordinary corn starch which make it easier and less expensive to process.

Several waxy barleys are described in the prior art, for example in our publications in Cereal Chemistry, 53 (2) pages 174–180, (1975), and Cereal Chemistry, 55, (2), pages 127–137, (1977), as well as our prior U.S. Pat. Nos. 4,042,414, issued Aug. 16, 1977, 4,054,671, issued Oct. 18, 1977 and 4,116,770, issued Sept. 26, 1978. These waxy barleys are produced by cross-breeding barley varieties having different genes as described in these publications. These publications and prior patents describe a barley species which is self-liquifying (Washonupana) and other waxy barleys (Wapana and Waxy Oderbrucker). The disclosures of these publications are hereby incorporated by reference, especially the disclosures which compare waxy barleys with normal barleys. Other species of waxy barleys which may be used as starting materials in the process of the present invention include Watan, Wabet, Washonutan, Washonubet, Wanutan and Wanupana. It should be noted that waxy barleys are usually named with the prefix "wa-", and normally contain about 98–99 wt.% of amylopectin. It should be understood that the waxy barley starting material is not limited to those named herein.

Figure 1:
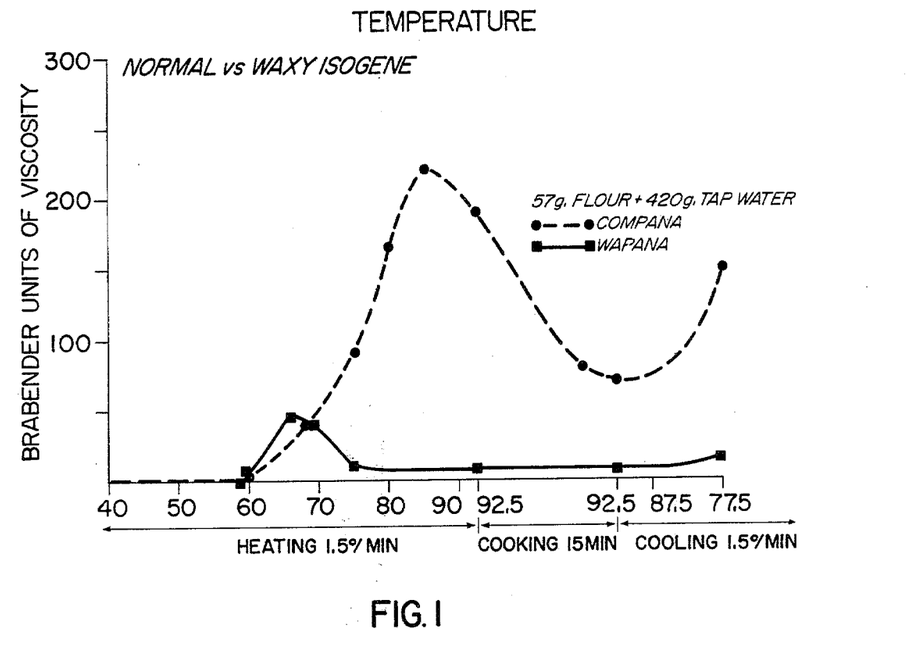
FIGS. 1, 2 and 3 are Brabender curves showing the distinction between the waxy barley flours used as the starting materials in this invention and normal barley flours.
Figure 2:
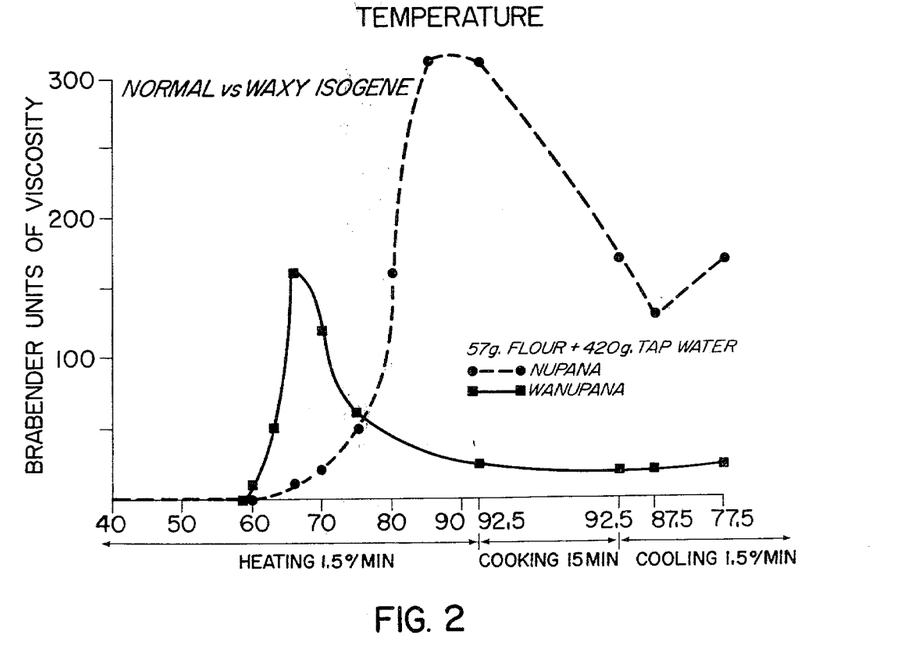
Figure 3:
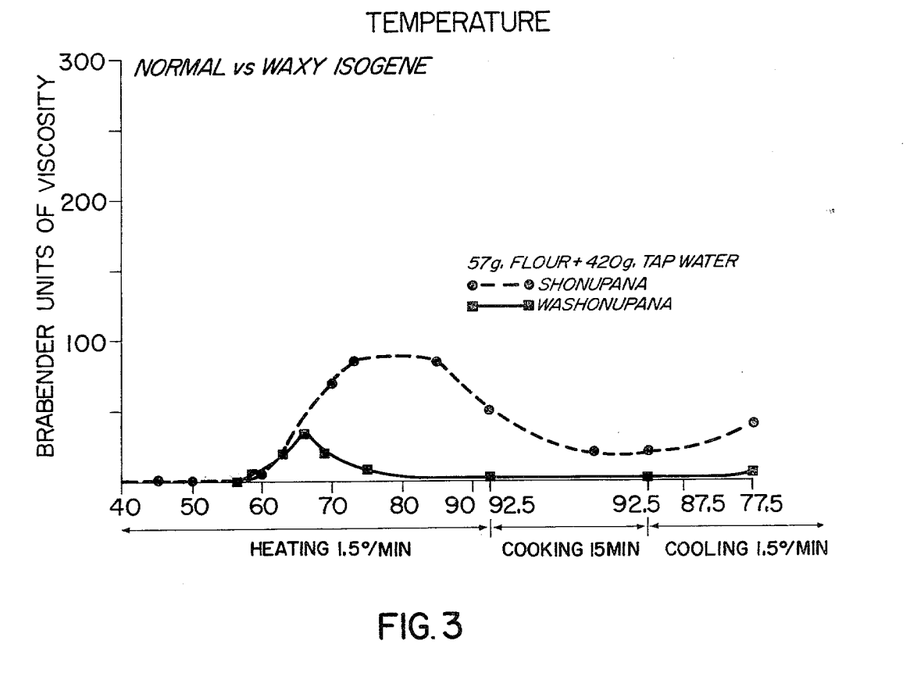

The differences between normal barley and the waxy barleys used in this invention are dramatized in FIGS. 1, 2 and 3 which are Brabender curves of the waxy barleys as compared with normal barleys. These curves show the Brabender units of viscosity which are determined as a result of heating different varieties of waxy and normal barley. In FIG. 1, Wapana, is compared with Compana; in FIG. 2, Wanupana is compared with Nupana; and in FIG. 3, Washonupana is compared with Shonupana. A comparison of the viscosities of the waxy varieties as compared to the normal barley varieties clearly show distinct differences in the Brabender unit of viscosity at the different temperatures.

Obviously, any equivalent starting material may also be employed providing that it is a waxy type product which contains less than about 8% amylose, or alternatively, contains at least about 92% amylopectin. It should be noted that a normal barley contains about 72–80% of amylopectin and the major difference between the waxy and the normal barley is found in the amylopectin content.

The process of the present invention produces a number of major products from the waxy barley starting material through a series of novel processing steps. These products may be broadly described as bran, starch, a feed grade product containing about 20 to 25% protein, a food grade product containing about 70 to 78% protein, a food grade product containing above about 80% protein, mixures of the proteins, a syrup containing in excess of 60% maltose, a high carbohydrate soluble fraction or a mill water by-product suitable for fermentation to an alcohol, and a carbohydrate gum suitable for a food thickener. Alternative products may also be produced. For example, if the low protein feed-grade product is combined with a high carbohydrate soluble fraction, also referred to herein as mill water, and this is combined with the wash waters from the starch and protein processing steps, subsequent frementation of the mixture by conventional methods will produce alcohol and/or Torula yeast with the by-product or dry distillers solubles similar in consistency to the product obtained when one ferments sugar from corn. The alcohol is of course valuable in many areas and particularly for combination with gasoline in the modern fuel sometimes referred to as "Gasohol".

The maltose syrup concentrate can be catalytically reduced to produce maltitol which is a commercial sweetener and could be considered as an optical product to be produced from the barley in addition to those named above. With the distillers solubles, yeast, alcohol and maltitol, as well as beta-glucan, this represents a large number of potential commercial products to be recovered from the barley grain. In view of the limited use of barley heretofore, this represents an outstanding contribution to the art of processing barley grain.

Of the several products produced, the bran is useful as a food supplement, particularly with current emphasis on fiber in the diet. The products low in protein content could, of course, be used as animal feeds whereas the high protein containing materials are, of course, useful in various major markets as a substitute for vital gluten which is obtained from wheat. It should be noted that the maltose syrup and the high protein products obtained from the barley according to the present invention are considered to be commercially attractive products having novel physical and chemical characteristics.

The maltose syrup in essence contains in excess of 60% maltose and less than 5% dextrose and with proper concentration, may contain up to 80% solids. Thus, this type of product is highly desirable and is useful in bakery and dairy products such as cereal, sweeteners, ice cream, and brewing operations as well as hard candy products. For example, in the ice cream industry, the maltose syrup is useful in providing texture for body and crystallinity control.

These products are produced by a multistep procedure comprising processing of the barley grain. These processes are broadly described in FIG. 4 with the starch separation and conversion processes more specifically described in FIG. 5. The initial step comprises selection of the starting waxy barley grain and cleaning at 1 to remove inert particles, dirt and the like, prior to processing, which are passed to waste or by-product recovery by line 2. The grain is then removed by line 2 and subjected to conditioning and milling at 5 to remove hulls if necessary, and to condition by the injection of a little moisture as by the introduction of steam at 4. It should be understood that in this step, either the hulless barley or barley with hulls can be introduced but any hulls present are preferably removed. In the milling operation of this step, most of the bran and a portion of the germ are removed by this stage to result in a crude flour product. The milling stage is preferably carried out by dry grinding using for example a simple wheat flour mill. The amount of moisture to be introduced is that amount necessary to assist in conditioning and milling of the product. The crude flour is removed from the conditioning and milling step by line 7 and transferred to a mixing tank 8 where sufficient water is introduced by line 9 to provide a slurry that can be easily handled. The water is fresh makeup water and/or process recycle water obtained from source 10-a and 10-b introduced by line 11 and line 9. In general, about 3-5 parts of water per part of flour are present in the mixing tank. A small amount of enzyme is introduced by line 11a in order to reduce the viscosity caused by the presence of beta-glucan. In the mixing operation or stage 8, milling, screening and the initial separation and removal by ine 12 of a low-grade protein is made, the protein being removed to by-product recovery. This feature is specifically described with respect to FIG. 5.

The starch slurry is then removed by line 13 to what may be broadly described as a starch separation stage at 14. The mill water is removed by line 15 to by-product recovery. The starch granules at this point are centrifuged and removed by line 16 to a conversion and refining stage 17 where, with adjustment of solids contents by water introductions via line 18, and the introduction of additional enzyme or green malt as required by line 19, novel protein products and maltose are obtained. The starch separations and conversion and refining operations are more specifically described in FIG. 5.

In this step, proteins are released and maltose is produced in this step by the addition of the enzyme or green malt which contains beta-glucanase which will partially hydrolyze the beta-glucans contained in the barley starch. After the production of these substances the proteins released are removed by line 20 to by-product recovery and further processing. The syrup which contains the maltose is removed by line 21 to produce recovery 22. Condensate from the conversion and refining procedures are removed by line 23. The wash waters and other by-product liquors are removed by line 24 and recycled.

The by-products recovered from the starch separation 14, and conversion and refining stage 17, are passed to by-product recovery 25 as shown where appropriate processing takes place to recover the several by-products from the operation. The by-product procedures are discussed more specifically with respect to FIG. 5. In general, solids contents are adjusted, additional enzyme is added to substantially complete the hydrolysis of the remaining beta-glucans, and together with separating techniques, result in removal of at least one protein product high in protein content at 30 by line 29. As may be seen, steam for heating and solids content adjustment of the fermentable fiber cake and protein cake are added by lines 26, 27 and 28, respectively. In addition, a mill water or carbohydrate water is removed by line 31 to recovery 32 which is a fermentable mixture suitable for conversion by conventional fermentation procedures to alcohol or other products. The fiber cake is removed from the system by line 33 to cake recovery 34 and roughage such as hulls and cracked grain are removed by line 35 to recovery 36. Condensate is removed by line 37 and may be recycled by line 37. Mother liquors and wash waters from this by-product recovery 25 are recycled as necessary or required via line 38. Beta-glucan is removed by line 39 and recovered at 39a.

Figure 4:
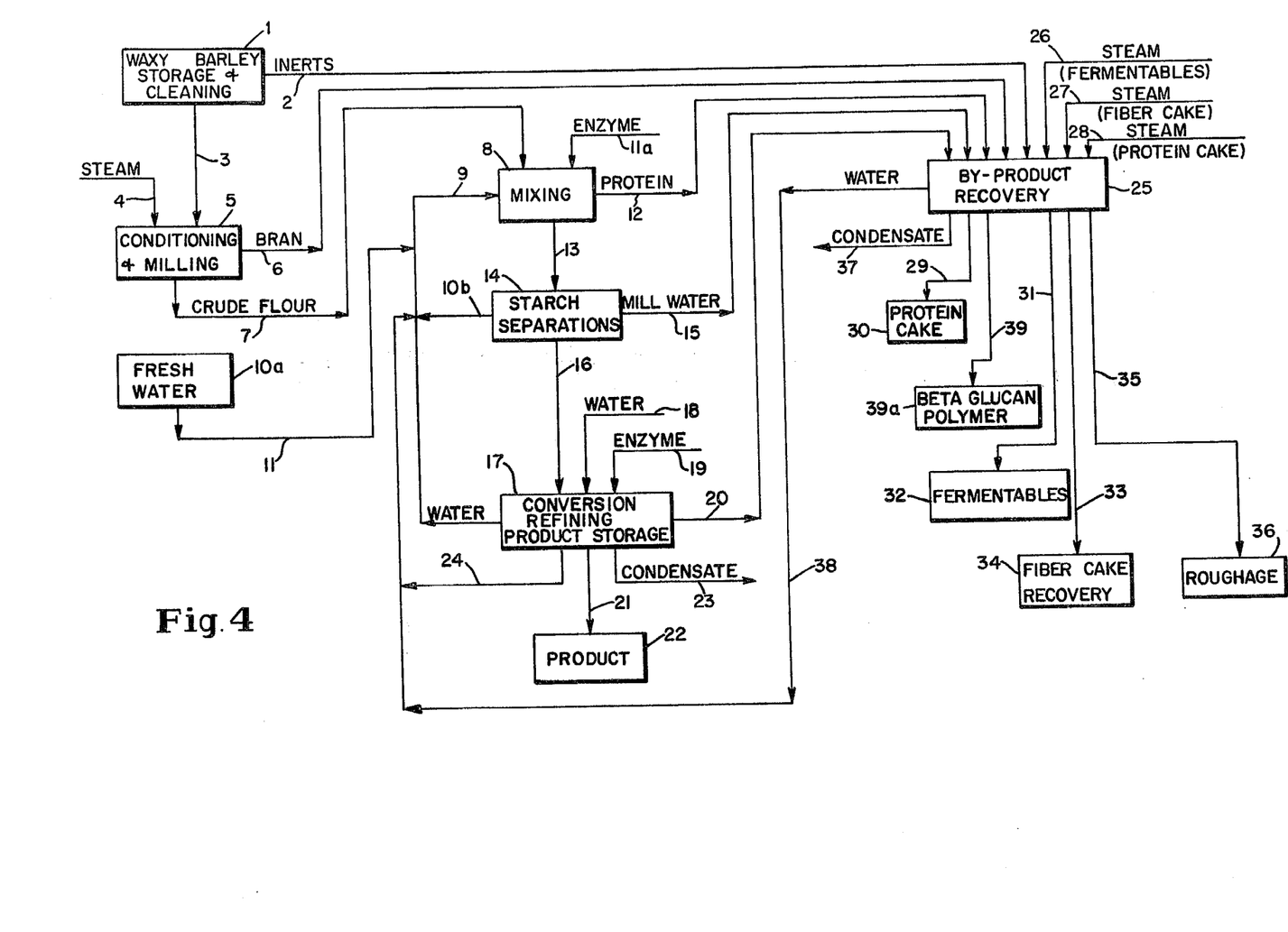
FIG. 4 shows a complete schematic flow sheet for a commercial processing system of the present invention.
Figure 5:
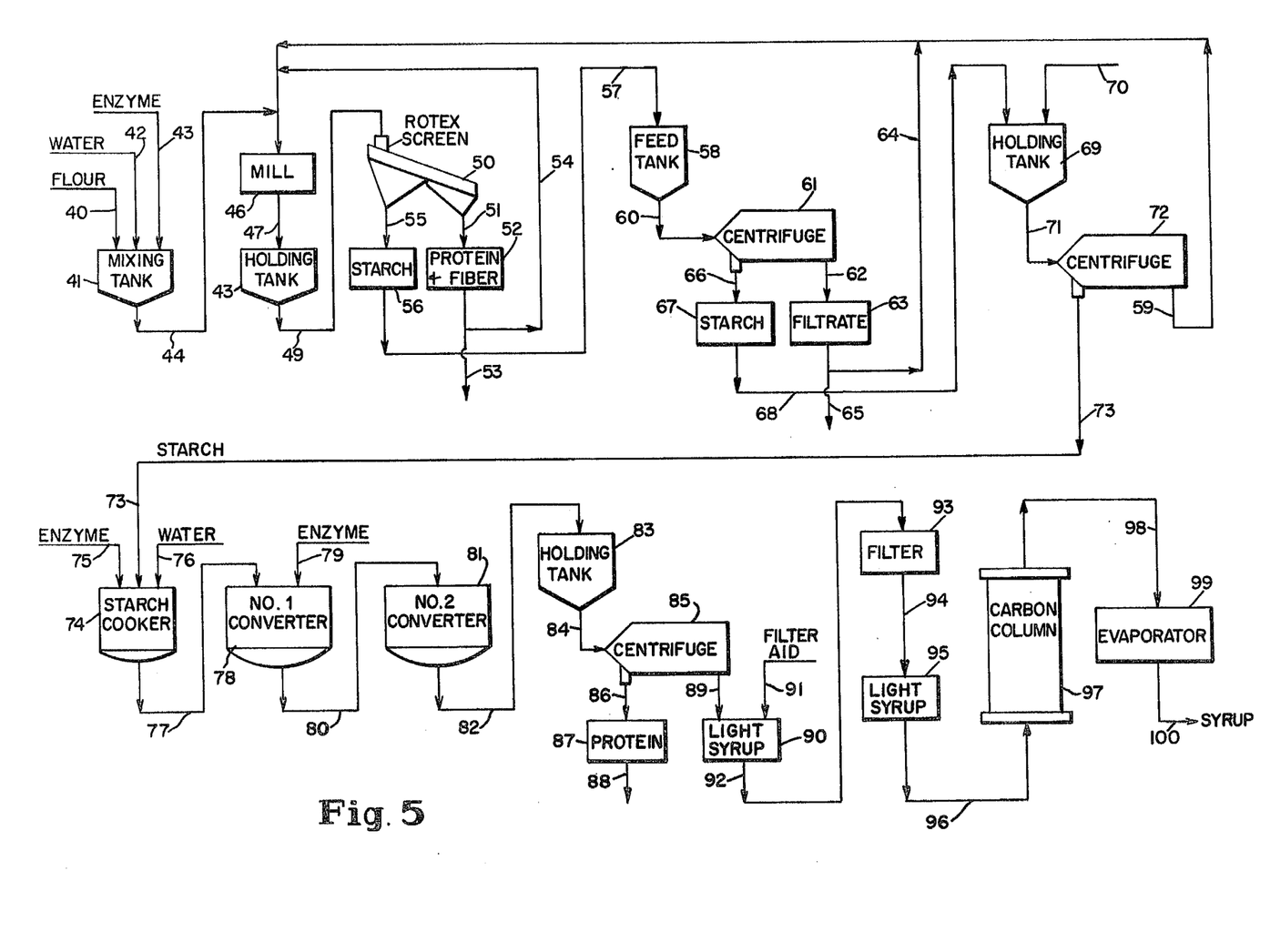
FIG. 5 is a flowsheet showing details of the starch separations and conversions and recovery of products.

The schematic diagram of FIG. 4 shows the broad steps and parameters of the process of this invention by which the several useful products are obtained. FIG. 5, however, sets forth specific embodiments for conducting the process, particularly with respect to the starch separations and conversions and product recovery, and alternative procedures.

Referring now to FIG. 5 which in essence is an actual pilot plant run, it will be seen that the process begins with the mixing step and is followed by the starch separation, conversion, and product recoveries occurring thereafter. In the diagram of FIG. 5, the raw barley material, after the bran and inerts have been removed, is introduced by line 40 into mixing tank 41 provided with agitation, together with sufficient water by line 42 to convert the crude barley flour to a thin paste. Generally, about 3 to 5 parts of water per part of flour are added. At this stage, prior to grinding, there is also added a sufficient amount of an enzyme, preferably green barley malt by line 43, to partially hydrolyze the beta-glucans present and to reduce the viscosity to workable levels. In general, it may be said that there is added sufficient green barley malt or equivalent material at this stage to lower the viscosity of the slurry to a workable viscosity in about 1 hours time. The enzyme or green barley malt contains beta-glucanase which is used to at least partially hydrolyze the beta-glucans present in the barley. The beta-glucans are substances which make the barley difficult to work with and it is therefore expedient to partially hydrolyze and remove them at this stage of the process.

The green malt added is preferably a waxy barley green malt since one needs the debrancher and all the beta-glucanase that can be added in order to partially hydrolyze as much of the beta-glucans as possible without the addition of any normal barley starch which has a higher pasting temperature. Dry malt is operable but a substantially larger quantity would be required and maltose yields would be less. By green malt is meant that it is freshly made and not kilned malt. It is also possible to add a commercial bacterial amylase or enzyme rather than the green malt but the material to be added will be dictated by economics and should be based on the least amount of material necessary to saccharify the starch and which is effective to remove the glucans. Products which can be used in place of the green malt are a commercial product sold as Cereflo 200 L which is an industrial bacterial beta-glucanase preparation produced by fermentation which will thin the starch and hydrolyze the beta-glucan and Wallersteins Malt Enzyme PF which will furnish the amylases to conversion of thinned starch to sugars available from Wallerstein Company.

The resulting slurry is then removed by line 44 and subjected to a milling operation by passing through a conventional mill such as burr mill 46. In the actual operation this process is repeated two more times. The burr mill is a conventional device that is simply effective to grind the grain. The ground material from the mill 46 is transferred by line 47 to a holding tank 48 which is provided with agitation to maintain the slurry in suspension. The mixture is then pumped via line 49 to a vibrating Rotex screen where a separation is made between the starch product and the protein. At this stage the protein is continually removed by line 51 to container 52. This protein material is recycled two more times in sequence with the previously described milling operation until the protein is essentially free of starch. The residual protein-fiber residue is washed and dried producing a barley gluten feed containing 20–25 weight percent protein content. The protein-fiber residue is recovered at line 53. Process water is recycled to milling by line 54.

The starch is removed from screen 50 by line 55 to container 56 and then passed to the feed tank 58 for centrifuge by line 57.

The resulting starch slurry is then passed by line 60 to centrifuge 61 or equivalent separator to obtain starch with 40–60% by weight starch solids and a filtrate solution. The filtrate is removed by line 62 to container 63 and comprises mill water which is continuously reused by recycle to milling through line 64 until maximum solids, usually about 15%, are obtained. The mill waters, which are suitable for subjecting to he conventional fermentation for the production of alcohol and distillers dry solubles, are recovered at line 65.

The total recovered starch in line 66 from centrifuge 61 is transferred to container 67, is washed, and then transferred by line 68 to holding tank 69. Water may be added by line 70 as necessary. The starch is removed at line 71 to centrifuge 72 where the starch is washed one more time with the wash water being recycled via line 59 to mill 46.

The refined starch is then passed by line 73 to a jacketed agitated cooking vessel 74 for starch conversion. Water is added via line 76 to obtain a starch solids concentration in the range of 25–35 weight percent basis, most preferably about 30%.

At this point the pH of the starch in the cooker should be in the range of 5.5 to 6.0, preferably about 5.6–5.8, but it may be necessary to adjust the pH to within the desired range as by the addition of sodium hydroxide. Also, to the resulting mixture is added about 0.5% by weight of green malt based on the dry weight of starch by line 75 and the contents are constantly agitated. The pH-adjusted mixture is then subjected to heating in the temperature range of about 75°–76° C. until the starch dissolves and there are no starch granules remaining in the mixture. This normally requires a period of from about 5–15 minutes. Additional water may be added if necessary through line 76. It is important that the temperature be maintained relatively near to the 75°–76° C. range because if the temperature goes too high, it could adversely affect the waxy barley gluten.

At this point, the mixture is removed from the cooker 74 by line 77 and passed to the No. 1 converter 78. The temperature in converter No. 1 is reduced to about 40° C. and a further portion of about 0.5 wt % green malt is added through line 79. In this stage the solution is held at a temperature of about 40° C. for about 1 to 4 hours with continuous agitation. While it is theorized that in converter No. 1, the debrancher in the green malt is effective in debranching the amylopectin and in partial hydrolysis of beta-glucan, Applicants do not intend to be bound by this theoretical explanation as a sole basis for its action.

The resulting solution is then passed by line 80 to No. 2 converter 81 where the mixture is maintained at a temperature of 50°–70° C. for about ½ to 2 hours. Preferably, the solution is maintained at about 60° C. for 1 hour or sufficiently long for the viscosity to become low enough to centrifuge the mixture. At this stage the gluten from the barley will be released and the mixture is then centrifuged to remove the gluten from the syrup filtrate. To do this, the mixture is passed by line 82 to holding tank 83 and then via line 84 to centrifuge 85. In the centrifuge, the crude protein is removed by line 86 to container 87, and after washing and drying, recovered at 88 where it will be found to contain about 75–80% protein.

In an alternative embodiment, (not shown), after centrifuging and removal of crude gluten, the mixture may be returned to Converter No. 2 and held for an additional time to lower the viscosity, so that the beta-glucan can be removed with a supercentrifuge. The resulting product can be spray dried to produce a carbohydrate gum in yields of 1–3% of initial flour weight. The carbohydrate gum is believed to be a waxy barley beta-glucan polymer consisting of a series of glucose units hooked together through a beta-linkage, and is probably a mixture of polymers. The gum is characterized by its ability to produce a high viscosity in relatively dilute aqueous solutions, similar to lower or medium viscosity cellulose gums. The gum product is generally tasteless and its gum characteristics make it suitable as a low calorie thickening agent for the food industry such as in salad dressings.

The separated crude gluten is washed with water and solubilized in an aqueous solution of lactic acid having a pH of about 4.0. The suspension is then centrifuged and on freeze drying a 66.5% protein product is obtained not having the characteristic properties of gluten. This fraction makes up 38% of the total protein recovered at 88. This protein has a greet affinity for water and will produce a gel containing 85% water. The pH is then adjusted to 6.0–6.5 with sodium hydroxide, and centrifuged to remove gluten which on freeze drying yields a product containing 89.3% protein. This fraction makes up 59% of the protein recovered at line 88.

In the meantime, the light syrup obtained from the centrifuge via line 89, which is still at a temperature of about 60° C., is held from 12–48 hours until maximum maltose content is obtained and then a filter aid is added to the resulting mixture by line 91 and the mixture removed by line 92 and filtered at 93 to remove residual solids. The resulting sparkling light tan syrup is then removed by line 94 from the filter 93 to container 95 and then subjected to decoloration by passing through line 96 to a carbon column 97 to obtain a clear syrup. The clear syrup is passed by line 98 to concentrator 99 where the syrup is concentrated by heating and recovered at 100. The resulting concentrated syrup contains about 2–5% glucose, about 60–65% maltose, with a total solids content in the range of about 80%. Preferably, concentration is carried out by continuously feeding the syrup to multi-effect spray film evaporators for concentration to the final product containing about 80% solids. A recycle loop may be provided for light syrup that does not meet with quality control standards for clarity or composition. This is the maltose syrup product produced in accordance with the invention.

It will be appreciated that this process produces a number of major waxy barley products including bran, the several grades of protein, the high maltose containing syrup, the fermentable product and carbohydrate gum. The manufacture and recovery of these products from waxy barley thus provides a wide variety of products from a grain which heretofore has not been used for any commercial products.

The following examples are presented to illustrate specific embodiments and best modes of the process of the present invention. However, the process of the invention is not to be considered as limited to the embodiments of these examples. In the examples and throughout the specification, parts are by weight unless otherwise indicated.

(6) Filter through a 45 Millipore filter.

Samples for total carbohydrate (Phenol/$H_2SO_4$ using a glucose standard) and glucose (glucose oxidase method) were taken after step (2) above.

A portion of each syrup was tested for dextrin color by layering aqueous $I_2$/KI onto the syrup. The 1 hr. and 2 hr. samples stained dark opaque brown; the 4 hour sample stained dark brown, but did transmit some light; the 12½ hr. sample had only a faint trace of iodine stain.

No provision was made for evaporation loss, so the total carbohydrate reflects both changes due to solubilization of starch/dextrins/glucans and also evaporation of water. After the 48 hr. sample was taken, an arbitrary amount of water was added to thin the syrup as it was becoming too heavy (46.5% total solids). The values for total carbohydrate on the following table were measured using a glucose standard and expressed as maltose. The % glucose is present of total carbohydrate based on wet chemistry.

| Time After Enzyme Addition | Measured D.E.*[1] | Calculated (Theoretical) D.E. | Glucose % | $DP_2$%*[2] | $DP_3$%*[3] | Highers % | Total Carbohydrate Expressed as Maltose (mg/ml) |
|---|---|---|---|---|---|---|---|
| 1 Hr. | 33.3 | 42.7 | 1.1 | 74.5 | 6.3 | 18.1 | 291 |
| 2 Hr. | 31.1 | 29.2 | 1.1 | 39.9 | 3.8 | 55.2 | 300 |
| 4 Hr. | 33.8 | 31.6 | 1.2 | 45.7 | 4.4 | 48.7 | 309 |
| 12½ Hr. | 38.2 | 36.7 | 2.4 | 55.6 | 6.1 | 35.9 | 331 |
| 24 Hr. | 38.9 | 41.0 | 3.7 | 63.6 | 6.9 | 25.8 | 350 |
| 36 Hr. | 39.6 | 42.3 | 4.1 | 64.9 | 8.9 | 22.1 | 406 |
| 48 Hr. | — | 39.4 | 4.6 | 57.3 | 6.7 | 31.4 | 462 |
| 60½ Hr. | 40.7 | 40.6 | 5.0 | 59.1 | 7.5 | 28.4 | 416 |

[1] D.E. - Dextrose equivalent
[2] $DP_2$ - Degree of polymerization - two glucose units
[3] $DP_3$ - Degree of polymerization - Three glucose units

EXAMPLE I

Starch Conversion—Ref. Actual Pilot Run

In this example, 0.5 wt. % waxy barley green malt was added to starch cooker 74 containing waxy barley Washnupana starch from centrifuge 72 added by line 73. Sufficient water was added by line 76 to make the mixture about 30% starch solids. The mixture was heated with agitation until the temperature reached 75° C. and held for 10 minutes. At this point the material was transferred by line 77 to converter No. 1 where the temperature was dropped to 40° C. and held at this temperature. An additional 0.5 wt. % of waxy barley green malt was added and the mixture continuously agitated. After 4 hours the mixture was transferred to converter No. 2 where it was maintained at 60° C. for the balance of the run. Samples were taken at various time intervals following the malt addition:

1 hour, 2 hours, 4 hours, 12½ hours, 24 hours, 36 hours, and 60½ hours. Each sample was cooled quickly by immersing the glass sample bottle (2 oz.) in running water at 3° C. The samples were prepared for HPLC analysis in the following manner:

(1) Centrifuge for 20 min at 16,300×g to remove protein, glucan, etc.

(2) Decant supernatant and place in boiling water bath for 30 minutes to inactivate enzymes (Note: There may be a short "burst" of enzyme activity as the refrigerated sample is heated.)

(3) Dilute sample 4-fold with doubly distilled water.

(4) Deionize with Amberlite MB-3 resin.

(5) Centrifuge for 15 min at 12,000×g.

As will be seen, this Example shows the increase in total carbohydrates expressed as maltose as the enzyme is given opportunity to work in effecting the conversion in the starch conversion stage. After 1 hour the total carbohydrates was 291 parts, whereas after 60½ hours the total carbohydrates had increased to 416 parts.

EXAMPLE II

This example is an experiment directed to barley bran fermentation wherein 150 grams of the bran, and 300 milliliters of water were combined into a very heavy paste and 0.15 milliliters of Cereflo 200 L were added while maintaining the bath at 70° C. While heating to 62° C. the mixture had thinned appreciably but on continued heating to 70° C., a paste was formed. The mixture was then cooled to 63° C. and 0.5 wt.% of waxy barley green malt added together with an additional 50 milliliters of water to decrease the pasty nature of the mixture.

After allowing to stand overnight at 60° C., the resulting mixture, which had liquified, was screened on a 115 mesh screen and pressed as dry as possible to obtain 187.3 grams of wet solids which dried to 66.2 grams. Baker's yeast was added to the liquid obtained from the pressed screenings. Correcting for sugars contained in the dried grain, a recovery of 21.5 grams of alcohol was obtained from the process. Calculations on this experiment are as follows:

The $CO_2$ loss was 20.4 grams and the total fermentables equal $CO_2$ loss+alcohol, which is equal to 20.5+20.4=41.9 grams.

The percent of barley bran fermentable =

-continued $$\frac{41.9g.}{(150g. - 18g. H_2O)} \times 100 = 31.6\% \text{ (db)}.$$

The nonfermentable solids from 150 grams of crude barley bran amounted to 39.2 grams.

EXAMPLE III

This example shows a batch process for the separation of proteins from the starch mixture. In this process the starch is separated and added to sufficient distilled water to provide a 30 wt.% starch slurry. Then 0.5 wt.% of waxy barley green malt is added based on the estimated dry weight of the starch. The resulting mixture is heated to 75° C. for 10 minutes. The mixture is then cooled to 40° C. and an additional 0.5 wt.% waxy barley green malt is added and held for 3 hours at 40° C. The mixture is then heated to 60° C. and held until the viscosity, as measured by a 100 milliliter pipette, was 10 seconds or less, which in this case required 1 hour. The resulting mixture was centrifuged on the Bird centrifuge and a protein removed which appeared much dryer than when removed at the end of the initial conversion time. The protein was washed in water to remove enzymes and sugars, frozen and stored. It was found to have elastic properties and to be chewable.

The protein was solubilized at a pH of 4 with lactic acid solution, centrifuged to remove insoluble protein and reprecipitated by adjusting the pH to 6.5 with sodium hydroxide. The protein still maintained its elastic properties. A portion of the protein was dried in a vacuum oven, and this material, when ground and mixed with water, again hydrated and formed an elastic material. Therefore, the characteristics and properties indicate that it is a gluten product. A more refined product is obtained by dissolving in lactic acid, centrifuging to remove any suspended material and reprecipitating followed by freeze drying the product.

EXAMPLE IV

Using the system described in FIGS. 4 and 5 in this embodiment, the grain selected is Washonupana waxy barley with the total charge to the system being 643.9 parts of dry barley with 87.8 parts of water. After cleaning, to remove straw and roughage, the resulting mixture contains 640.9 parts of barley and 87.1 parts of water and this mixture is then subjected to conditioning by the addition of 1600 lbs/hr. of steam and 500 lbs/hr. of water with the bran and a part of the germ being removed to by-product recovery. The resulting crude flour contains 564 parts of flour and 61 parts of water and is then passed to mixing where 987 parts of water and 0.5 wt.% of green Washnupana waxy barley malt are added to the mixture to hydrolyze beta-glucans present in the barley. After 1 hour, the milled product is screened and a screen residue removed from the system which analyzes as 21.0 wt.% protein, 5.1% moisture, 3.1% ether extractables, 2.5% ash and 7.7% crude fiber. The protein residue is washed, centrifuged, and betaglucan separated.

The crude starch removed from the mixing operation comprises 444.4 parts of starch and 943.6 parts of water and analyzes as containing 17.4% protein, 6.4% moisture, 1.9% ether extractables, 0.76% ash and 0.31% fiber.

The starch portion is washed and then centrifuged and a separation made between the starch granules and the filtrate. The filtrate is removed on the third pass and comprises process liquids or mill water in condition for fermentation to produce alcohol and distiller dry solubles.

The starch fraction, which comprises a mixture of 376.1 parts of starch granules and 220.9 parts of water, is passed to the conversion stage in a stirred container, and the pH is adjusted to a range of 5.6 to 5.8 by the addition of sodium hydroxide. Sufficient water is added to the mixture to bring the solids content to 30 wt.% and an additional 0.5 wt.% waxy barley green malt is added to thin the starch while heating the mixture to 75°–76° C. for 10 minutes. The amount of water added at this point is 334 parts.

After heating for 10 minutes the starch dissolves and the solution is then cooled to 40° C. and held for 4 hours with the addition of a further 0.5 wt.% of waxy barley green malt under continuous agitation. It is then heated to 60° C. and held until the viscosity decreases sufficiently to centrifuge. The mixture is then centrifuged to separate crude gluten from the light syrup. The syrup portion is returned to the holding tank at 60° C. for 1 hour and then supercentrifuged to remove the beta glucan gum. After separation of the beta glucan gum the syrup is returned to converter No. 2 and held until optimum maltose content is achieved. The crude gluten is washed with water, and dispersed in an aqueous solution of lactic acid at a pH of 4.0 which dissolves the gluten. The insoluble protein is removed by centrifugation and the solubilized gluten precipitated by adjusting the pH to 6.0–6.5 with sodium hydroxide. This material is freeze dried to produce a gluten product containing 89.3% protein and makes up 59% of the total crude gluten fraction. The lactic acid insoluble fraction makes up 38% by weight of the total crude gluten protein and on freeze drying contained 66.5% protein. This protein shows a high affinity for water as the freeze dried material will readily form a gel containing 85% water.

In the meantime, to the light syrup removed from the centrifuge, while still at 60° C., is added a small amount of the filter aid and the mixture subjected to filtration. The resulting light syrup is sparkling light tan in color and is then subjected to decolorizing in a carbon column and the resulting clear syrup was subjected to concentration in a multi-effect falling film evaporator to provide a finished product containing 80% solids which analyzes at 60–65 wt.% maltose, and 2–5% glucose.

The analysis described in the specific embodiments of this application were based on standard tests of the Association of Official Analytical Chemists as set forth in "Official Methods of Analysis", 12th Edition. The specific tests used included the following tests:

Protein—Test No. 7.016, page 130;
Ether Insolubles (Crude Fat)—Test No. 7.045, page 135;
Crude Fiber—Tests No. 7.05–7.054, pages 136–137;
Ash—Test No. 7.010, page 130;
Moisture—Test No. 7.003, page 129.

The invention has been described herein by reference to certain preferred embodiments. However, as obvious variations thereon will become apparent to those skilled in the art the invention is not to be considered as limited thereto.

What is claimed is:

1. A process for the production of protein products and maltose syrup from flour obtained from a waxy barley grain, the steps of the process comprising:

(a) obtaining a waxy barley flour from waxy barley grain and mixing with sufficient water to form a paste;
(b) adding to the paste a beta-glucanase-containing enzyme in a sufficient amount to thin the paste and form a slurry and at least partially hydrolyze beta-glucans contained in the flour to place the beta-glucans in a form suitable for separation from the starch, and then subjecting the slurry to grinding;
(c) removing the ground slurry to a holding tank provided with agitation for a sufficient time period for the enzyme to at least partially hydrolyze beta-glucans contained in the mixture and release protein solids from solution, and thereby form a resulting suspension containing crude starch, protein solids and fiber;
(d) subjecting the suspension to a solids separation step based on particle size by which the protein solids and fiber products are substantially removed from the suspension to provide a starch suspension;
(e) adjusting the solids content of the starch suspension to about 40-60 wt. % starch solids by removal of excess liquid which comprises a fermentable mill water;
(f) adding sufficient water to form a 25-35 weight percent solids suspension of the starch, and adding to said suspension additional enzyme which contains at least amylase in a sufficient amount to at least partially hydrolyze beta-glucans contained in the starch and at least partially hydrolyze the starch so as to release proteins and to form maltose and produce a resulting mixture containing these components;
(g) heating the resulting mixture to a temperature at about 75°-76° C. range for a sufficient period for the starch to dissolve and so that no starch granules remain in the resulting starch solution;
(h) cooling the resulting solution and adding a further portion of an enzyme which contains at least amylase, and agitating for a sufficient time to effect additional starch conversion, release protein and form maltose, and produce a resulting mixture of these components;
(i) heating the resulting mixture at a temperature of about 50° C. to 70° C. to substantially complete starch conversion, and form a mixture of protein solids in maltose syrup; and
(j) separating and recovering the protein solids and a liquid comprising a maltose syrup.

2. A process according to claim 1 wherein the waxy barley grain from which the flour is produced contains at least about 92% amylopectin.

3. A process according to claim 2 wherein the waxy barley flour is obtained from a barley grain selected from the group consisting of Washonupana, Washonutan, Washonubet, Wanupana, Wanutan, Wanubet, Wapana, Watson, Wabet, and Waxy Oderbrucker.

4. A process according to claim 1 wherein the waxy barley flour is obtained from the waxy barley grain by cleaning and milling the grain to remove most of the bran and produce the flour.

5. A process according to claim 1 wherein about 0.5% by weight of the enzyme, based on the weight of the solids, is added to the mixture in each of steps (b), (f), and (h).

6. A process according to claim 5 wherein the enzyme is a waxy barley green malt.

7. A process according to claim 1 wherein the proteins are removed from the starch slurry in step (d) by separation on a screen, and are washed and dried to produce a barley gluten feed containing 20-25 weight percent of protein content.

8. A process according to claim 1 wherein the solution from step (g) is cooled to a temperature of about 40° C. in step (h), about 0.5 wt. % of enzyme based on the amount of starch is added to the starch solution, the mixture is held at a temperature in the range of about 40° C. for about 1-4 hours with agitation.

9. A process according to claim 8 wherein the temperature of the mixture is then raised in step (i) to about 60° C. for about 1 hour, and the resulting solids and solution which comprise crude gluten protein solids and maltose syrup solution, are separated, and recovered.

10. A process according to claim 9 wherein after separation of the solids, the syrup solution is returned to a stirred container, heated at a temperature of about 60° C. for 1 to 2 hours and then subjected to supercentrifugation to separate beta-glucan protein solids from liquids comprising a light maltose syrup product.

11. A process according to claim 10 wherein the beta-glucan protein solids are then dried to form a carbohydrate gum.

12. A process according to claim 10 wherein the crude protein solids product is washed with water, dispersed in an aqueous solution of lactic acid and the lactic acid insolubles are removed from the solution, which insolubles comprise a gel, and freeze drying the gel to yield a product containing about 60-70 wt. % of protein.

13. A process according to claim 10 wherein the lactic acid solution remaining after removal of insolubles, is treated by adjusting the pH to 6.0 to 6.5, and the resulting precipitated protein solids are freeze-dried to produce a gluten product containing at least about 80 wt. % protein.

14. A process according to claim 1 wherein the maltose syrup recovered from step (j) is decolorized and then subjected to concentration to produce a concentrated maltose syrup comprising at least about 60% maltose.

15. A process for the production of protein products and maltose syrup from starch obtained from waxy barley by conversion of components in the starch to remove proteins and form maltose, the steps of the process comprising:
(a) forming a 25-35 weight percent mixture of waxy barley starch solids in water, at least a portion of beta-glucan protein solids having been removed from the starch;
(b) adding to said mixture an enzyme containing at least amylase in a sufficient amount to at least partially hydrolyze beta-glucans contained in the starch so as to release proteins and at least partially hydrolyze the starch and form maltose and produce a resulting mixture containing these components;
(c) heating the resulting mixture to a temperature at about the 75°-76° C. range from a sufficient period for the starch to dissolve and so that no starch granules remain in the resulting starch solution;
(d) cooling the resulting solution and adding a further portion of an enzyme which contains an amylase, and agitating for a sufficient time to effect additional starch conversion, to release proteins and form maltose, and produce a resulting mixture of these components;

(e) heating the resulting mixture at a temperature of about 50° C. to 70° C. to substantially complete starch conversion, and form a mixture of protein solids in maltose syrup; and (f) separating and recovering the protein solids and a liquid comprising a maltose syrup.

16. A process according to claim 15 wherein the waxy barley grain from which the starch is produced contains at least about 92% amylopectin.

17. A process according to claim 16 wherein the waxy barley starch is obtained from a barley grain selected from the group consisting of Washonupana, Washonutan, Washonubet, Wanupana, Wanutan, Wanubet, Wapana, Watan, Wabet, and Waxy Oderbrucker.

18. A process according to claim 15 wherein the waxy barley starch is obtained from the waxy barley grain by cleaning and milling the grain to remove most of the bran and produce flour from which the starch is obtained.

19. A process according to claim 15 wherein the enzyme is a waxy barley green malt.

20. A process according to claim 19 wherein about 0.5 wt. % of the enzyme, based on the weight of the solids, is added in each of steps (b) and (d).

21. A process according to claim 20 wherein in step (d), the solution is cooled to about 40° C., about 0.5 wt. % of enzyme is added to the starch solution, the mixture is held at a temperature in the range of about 40° C. for about 1–4 hours with agitation, and then in step (e) the temperature is raised to about 60° C. for about 1 hour, to complete starch conversion and to form a mixture comprising protein solids and maltose syrup.

22. A process according to claim 21 wherein after removal of the protein solids from the maltose syrup, the syrup is returned to a stirred container and held at about 60° C. for 1 to 2 hours to allow additional time for the enzyme to work, the resulting mixture is subjected to super-centrifugation to separate the crude gluten protein solids formed from liquids comprising a light maltose syrup product.

23. A process according to claim 22 wherein the beta-glucan protein solids are then dried to form a carbohydrate gum.

24. A process according to claim 22 wherein the crude protein solids product is washed with water, dispersed in an aqueous solution of lactic acid and the lactic acid insolubles are removed from the solution, which insolubles comprise a gel, and freeze drying the gel to yield a product containing about 60–70 wt. % of protein.

25. A process according to claim 22 wherein the lactic acid solution remaining after removal of insolubles, is treated by adjusting the pH to 6.0 to 6.5, and the resulting precipitated protein solids are freeze-dried to produce a gluten product containing at least about 80 wt. % protein.

26. A process for the production of protein products, maltose containing syrups, and a beta-glucan carbohydrate gum from flour obtained from a waxy barley grain, the steps of the process comprising:

(a) grinding waxy barley grain to produce a waxy barley flour and a bran product, and removing the bran; and mixing the waxy barley flour with sufficient water to form a paste;

(b) adding to the paste about 0.5 wt. percent of a waxy barley green malt enzyme, based on the weight of the solids, which amount is sufficient to thin the paste and form a slurry and at least partially hydrolyze beta-glucans contained in the flour to place the beta-glucans in a form suitable for separation from the starch and then subjecting the slurry to grinding;

(c) removing the ground slurry to a holding tank provided with agitation for a sufficient time period for the enzyme to at least partially hydrolyze beta-glucans contained in the mixture and release protein solids from solution, and thereby form a resulting suspension containing crude starch, protein solids and fiber;

(d) subjecting the suspension to a solids separation step based on particle size by which the protein solids and fiber products are substantially removed from the suspension to provide a starch suspension;

(e) adjusting the solids content of the starch suspension to about 40–60 wt. % starch solids by removal of excess liquid which comprises a fermentable mill water;

(f) adding sufficient water to form a 25–35 weight percent solids suspension of the starch, and adding to said suspension about 0.5 wt. % of a waxy barley green malt enzyme, said amount based on the weight of the solids, which amount is sufficient to at least partially hydrolyze beta-glucans contained in the starch and at least partially hydrolyze said starch so as to release proteins and form maltose and produce a resulting mixture containing these components;

(g) heating the resulting mixture to a temperature at about the 75°–76° C. range for a sufficient period for the starch to dissolve and so that no starch granules remain in the resulting starch solution;

(h) cooling the resulting solution to a temperature of about 40° C., adding a further about 0.5 wt. % portion of a waxy barley green malt enzyme, and agitating for a sufficient time to effect additional starch conversion, release protein and form maltose, and produce a resulting mixture of these components;

(i) heating the resulting mixture at a temperature of about 50° C. to 70° C. to substantially complete starch conversion, and form a mixture of protein solids in maltose syrup; and (j) separating and recovering the protein solids and a liquid comprising a maltose syrup.

27. A process according to claim 26 wherein the proteins are removed from the starch slurry in step (d) by separation on a screen, and are washed and dried to produce a barley gluten feed containing 20–25 weight percent of protein content.

28. A process according to claim 26 wherein the temperature of the mixture in step (i) is raised to about 60° C. for about 1 hour, and the resulting solids and solution which comprise crude gluten protein solids and maltose syrup solution, are separated, and recovered.

29. A process according to claim 28 wherein after separation of the solids, the syrup solution is returned to a stirred container, heated at a temperature of about 60° C. for 1 to 2 hours and then subjected to supercentrifugation to separate beta-glucan protein solids from liquids comprising a light maltose syrup product.

* * * * *